United States Patent
Stokes et al.

(10) Patent No.: US 8,827,973 B2
(45) Date of Patent: Sep. 9, 2014

(54) MEDICAL DRAPES, DEVICES, AND SYSTEMS EMPLOYING A HOLOGRAPHICALLY-FORMED POLYMER DISPERSED LIQUID CRYSTAL (H-PDLC) DEVICE

(75) Inventors: Benjamin Stokes, Ringwood (GB); Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 207 days.

(21) Appl. No.: 13/532,058

(22) Filed: Jun. 25, 2012

(65) Prior Publication Data
US 2012/0330252 A1 Dec. 27, 2012

Related U.S. Application Data

(60) Provisional application No. 61/500,945, filed on Jun. 24, 2011.

(51) Int. Cl.
*A61M 1/00* (2006.01)
*A61F 13/00* (2006.01)
*G01L 1/24* (2006.01)

(52) U.S. Cl.
CPC ..... *A61M 1/0088* (2013.01); *A61M 2205/0227* (2013.01); *A61M 2205/3331* (2013.01); *A61F 13/00068* (2013.01); *A61M 2205/3344* (2013.01); *A61M 1/0001* (2013.01); *G01L 1/24* (2013.01); *A61M 1/0029* (2013.01)
USPC ........................................................ 604/319

(58) Field of Classification Search
CPC ................ A61M 2205/15; A61M 2205/3331; A61M 2001/0025; A61M 2205/0227; A61M 2205/3344
USPC ........................................................ 604/319
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Susan Su
*Assistant Examiner* — Guy K Townsend

(57) ABSTRACT

A reduced-pressure medical treatment system for treating a tissue site on a patient includes a medical drape that has an holographically-formed polymer dispersed liquid crystal (H-PDLC) device that changes visual appearance when experiencing strain. The change in visual appearance of the H-PDLC device allows identification of the existence of strain and may allow a quantitative assessment of the range of stress involved. In other aspects, a dressing conduit connector, canister, and reduced-pressure interface use a holographically-formed polymer dispersed liquid crystal (H-PDLC) device to help determine the existence and perhaps the amount of stress experienced. Other systems, methods, and devices are presented.

26 Claims, 10 Drawing Sheets

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,477,469 A * | 11/1969 | Paley | 137/883 |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,872,050 A | 3/1975 | Benton et al. | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,971,068 A * | 11/1990 | Sahi | 600/576 |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,270,781 A * | 12/1993 | Singh et al. | 356/32 |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,778,236 B1 * | 8/2004 | Crawford et al. | 349/86 |
| 6,814,079 B2 | 11/2004 | Heaton et al. | |
| 6,840,915 B2 * | 1/2005 | Augustine | 602/2 |
| 8,287,461 B2 * | 10/2012 | MacDonald et al. | 600/549 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0097100 A1 | 5/2003 | Watson | |
| 2003/0144619 A1 * | 7/2003 | Augustine | 602/2 |
| 2003/0216732 A1 * | 11/2003 | Truckai et al. | 606/49 |
| 2005/0087021 A1 * | 4/2005 | Crawford et al. | 73/800 |
| 2007/0045588 A1 * | 3/2007 | Tsai et al. | 252/299.01 |
| 2008/0071214 A1 * | 3/2008 | Locke et al. | 604/111 |
| 2008/0281281 A1 * | 11/2008 | Meyer et al. | 604/313 |
| 2009/0124925 A1 * | 5/2009 | MacDonald et al. | 600/549 |
| 2010/0016767 A1 * | 1/2010 | Jones et al. | 601/10 |
| 2011/0245682 A1 * | 10/2011 | Robinson et al. | 600/473 |
| 2012/0330252 A1 * | 12/2012 | Stokes et al. | 604/318 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 102005014420 A1 | 9/2006 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |

(56) References Cited

FOREIGN PATENT DOCUMENTS

WO          99/13793        3/1999
WO     WO 01/92843 A2    12/2001

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukić, Ž Maksimović, Ð. . Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for corresponding PCT/US2012/043994, mailed Nov. 13, 2012.

* cited by examiner

MEDICAL DRAPES, DEVICES, AND SYSTEMS EMPLOYING A HOLOGRAPHICALLY-FORMED POLYMER DISPERSED LIQUID CRYSTAL (H-PDLC) DEVICE

RELATED APPLICATIONS

The present invention claims the benefit, under 35 USC §119(e), of the filing of U.S. Provisional Patent Application Ser. No. 61/500,945, entitled "Medical drapes, Devices, and Systems Employing a Holographically-Formed Polymer Dispersed Liquid Crystal (H-PDLL) Device," filed Jun. 24, 2011, which is incorporated herein by reference for all purposes.

FIELD

The present disclosure relates generally to medical treatment systems and, more particularly, but not by way of limitation, to medical drapes, dressings, devices and systems employing a holographically-formed polymer dispersed liquid crystal (H-PDLL) device that gives a visual indication of strain.

BACKGROUND

Wounds typically require care to heal properly. A wound may be treated and covered by a dressing. In more recent times, a wound may be treated using reduced pressure. Clinical studies and practice have shown that providing a reduced pressure in proximity to a tissue site, such as a wound, augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

Typically, reduced pressure is applied to tissue through a porous pad or other manifold device. Unless otherwise indicated, as used throughout this document, "or" does not require mutual exclusivity. The porous pad contains cells or pores or pathways that are capable of distributing reduced pressure to the tissue and channeling fluids that are drawn from the tissue site. The porous pad is typically covered by a drape that forms a seal. Drapes are also used in medical wound dressings for use without reduced pressure.

SUMMARY

According to an illustrative embodiment, a reduced-pressure treatment system for treating a tissue site on a patient includes a distribution manifold for disposing proximate to the tissue site, a drape for covering the distribution manifold and a portion of the patient's intact skin to form a sealed space, and a reduced-pressure source fluidly coupled to the sealed space. The drape comprises a holographically-formed polymer dispersed liquid crystal (H-PDLC) device having layers of liquid crystal (LC) droplets in a matrix polymer.

According to another illustrative embodiment, a method for treating a tissue site on a patient with reduced pressure includes disposing a distribution manifold proximate to the tissue site, and covering the distribution manifold and a portion of the patient's intact skin with a drape to form a sealed space. The drape comprises a holographically-formed polymer dispersed liquid crystal (H-PDLC) device. The method further includes delivering reduced pressure to the sealed space and monitoring the drape for any changes in visual appearance in the holographically-formed polymer dispersed liquid crystal (H-PDLC) device due to strain.

According to another illustrative embodiment, a dressing for covering a tissue site on a patient includes a drape for applying over the tissue site that changes visual appearance when subjected to strain. The drape comprises a holographically-formed polymer dispersed liquid crystal (H-PDLC) device having layers of liquid crystal (LC) droplets in a matrix polymer. The dressing further includes an adhesive for removably coupling the drape to the patient's skin.

According to another illustrative embodiment, a reduced-pressure interface for providing reduced pressure to a tissue site includes an interface body having a base and a suction head. The suction head includes a conduit opening for coupling to a reduced-pressure delivery conduit, a delivery opening for communicating reduced pressure to the tissue site, and a passageway fluidly coupling the conduit opening and the delivery opening. At least a portion of the interface body comprises a holographically-formed polymer dispersed liquid crystal (H-PDLC) device having layers of liquid crystal (LC) droplets in a matrix polymer.

According to another illustrative embodiment, a canister for receiving body fluids includes a canister body forming a fluid reservoir, an inlet for receiving a reduced-pressure delivery conduit, and at least one pressure-indicating device formed on the canister body that is activated to change visual appearances when experiencing strain within a first range. The pressure-indicating device comprises a window frame covered by a holographically-formed polymer dispersed liquid crystal (H-PDLC) device.

According to another illustrative embodiment, a conduit connector for connecting medical conduits includes a connector body. The connector body includes a chamber, an inlet for receiving a first conduit, and an outlet for receiving a second conduit. The conduit connector further includes a pressure-indicating device formed on the connector body. The pressure-indicating device comprises a window frame covered by a holographically-formed polymer dispersed liquid crystal (H-PDLC) device.

According to another illustrative embodiment, a method for treating a wound includes preparing the wound and covering the wound with a drape. The drape comprises a holographically-formed polymer dispersed liquid crystal (H-PDLC) device having layers of liquid crystal (LC) droplets in a matrix polymer. The drape is configured to change visual appearance when subjected to a strain greater than a threshold strain. The method further includes confirming that that the drape has not experienced a change in visual appearance indicative of a strain greater than the threshold strain.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

In caring for wounds with a dressing, it is desirable at times to qualitatively or quantitatively indicate strain in the dressing. The presence and magnitude of strain in the dressing, and in particular in a drape, can indicate a number of phenomenon. For example, in reduced pressure treatments strain can indicate the presence of reduced pressure, over-pressurization of a dressing during installation therapy, or over-stretching of the drape during application. Over-stretching the drape during application of the dressing on the patient can cause pain for the patient and ultimately may contribute to non-compliance. Over-stretching may also cause skin marking or irritation. For at least these reasons, a dressing is desired that visually indicates qualitatively or quantitatively the presence of strain.

Figure 1:
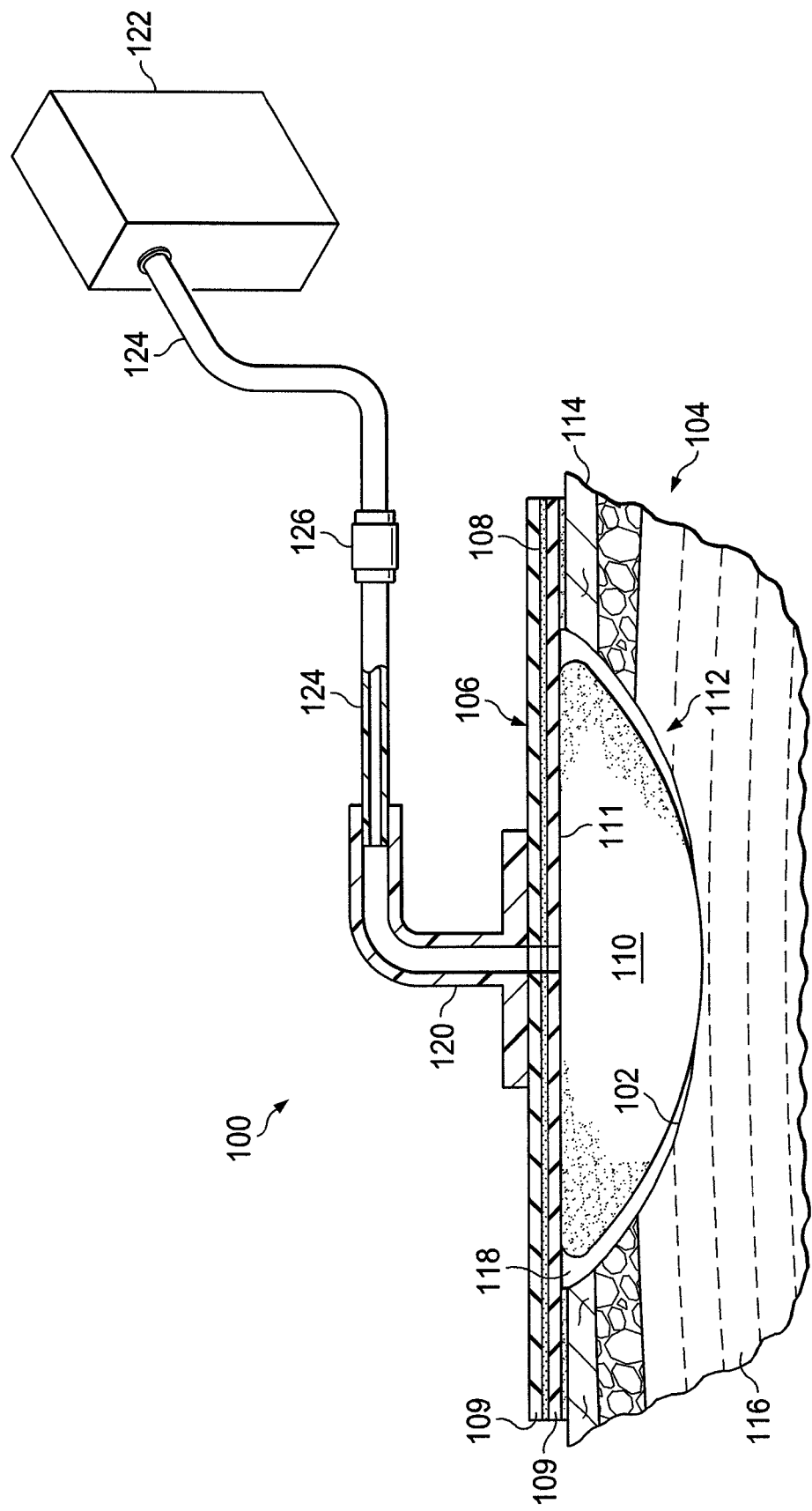
FIG. 1 is a schematic diagram, with a portion shown in cross section and a portion shown in perspective view, of an illustrative embodiment of a reduced-pressure treatment system for treating a tissue site on a patient.

Referring now to the drawings and initially and primarily to FIG. 1, a reduced-pressure treatment system 100 for treating a tissue site 102 on a patient 104 is presented. The reduced-pressure treatment system 100 includes a drape 106 that includes a holographically-formed polymer dispersed liquid crystal (H-PDLC) device 108. The H-PDLC device 108 has layers of liquid crystal (LC) droplets in a matrix polymer. The H-PDLC device 108 is typically a reflective strain gauge as will be described further below. The H-PDLC device 108 provides a visual indication of stress on the drape 106 by changing colors or otherwise changing visual appearances of ambient light that is reflected to an observer.

The H-PDLC device 108 is associated with the drape 106 and may be attached to one or more polymer layers 109 or may be sandwiched between two elastomeric layers, typically polymer layers 109, as shown or otherwise incorporated into the drape 106. The H-PDLC device 108 may be coextensive with the polymer layer or layers of the drape 106 or may only partially cover the other layers of the drape 106. For example, the H-PDLC device 108 may form a plurality of strips or a grid pattern that is attached to a polymer layer or that is sandwiched between polymer layers as an aspect of the drape 106. In one illustrative embodiment, the drape 106 has a surface area A and the H-PDLC device 108 covers 50 percent or less of A. The reduced coverage may help with vapor transmission rates through the drape 106.

The drape 106 may be any material that provides a fluid seal and is flexible. The drape 106 may be, for example, an impermeable or semi-permeable, elastomeric material. Examples of suitable elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of drape materials include a silicone drape, a 3M Tegaderm® drape, or a polyurethane (PU) drape such as one available from Avery Dennison Corporation of Pasadena, Calif.

The drape 106 includes an attachment device 113 (FIG. 2) on a patient-facing side 107 of the drape 106. The attachment device 113 may take numerous forms. For example, the attachment device 113 may be a medically-acceptable, pressure-sensitive adhesive that extends about a periphery, a portion, or the entire drape 106. As additional examples, the attachment device 113 may be a double-sided drape tape, paste, hydrocolloid, hydrogel or other sealing device or element.

Figure 2:
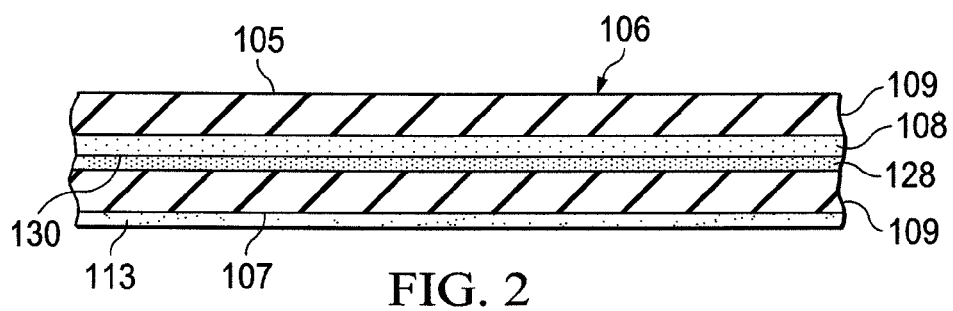
FIG. 2 is a schematic cross section of a portion of a drape according to one illustrative embodiment.

Referring now primarily to FIG. 2, the drape 106 may take numerous embodiments. In the illustrative embodiment shown, the H-PDLC device 108 is sandwiched or layered between two members of a plurality of polymer layers 109. In addition, a layer 128 that is an optional reflective layer may be on the patient-facing side 130 of the H-PDLC device 108 to make changes in the visual appearance of the H-PDLC device 108 easier to see from a point external to the drape 106. In still another optional alternative, the layer 128 may be a light-absorbing layer. In one embodiment, an optical reader (not shown), e.g., a photodiode, a spectrometer or other suitable instrument for observing a wavelength shift, or an analyzer for observing a polarization-dependent shift in the reflected light, may be associated with the drape 106 for monitoring electronically for any visual changes in the H-PDLC device 108. The drape 106 has a first side 105 and a second, patient-facing side 107.

Referring again primarily to FIG. 1, the drape 106 covers a distribution manifold 110, which is disposed proximate to the tissue site 102, e.g., a wound 112. The wound 112 is shown through the patient's skin 114 and into subcutaneous tissue 116. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue site 102 may include removal of fluids, e.g., exudate or ascites.

The drape 106 covers the distribution manifold 110 and a portion of the patient's intact skin 114 to form a sealed space 118. A reduced-pressure interface 120 may be fluidly coupled to the sealed space 118. The reduced-pressure interface 120 may be fluidly coupled to a reduced-pressure source 122 by a reduced-pressure delivery conduit 124. The reduced-pressure delivery conduit 124 may include one or more conduit connectors 126, which couple conduits to form an integral reduced-pressure delivery conduit 124.

The reduced-pressure source 122 may be any device for supplying a reduced pressure. For example, the reduced-pressure source 122 may be a vacuum pump, wall suction, micropump, or other source. The reduced-pressure source 122 typically includes a canister for receiving fluids. While the amount and nature of reduced pressure applied to a tissue site 102 will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). Alternatively or in addition, a reduced-pressure source may be included in the sealed space 118 and provide reduced pressure therein while discharging exhaust outside of the sealed space. For example, a micro-pump such as that shown in United States Patent Publication 2009/0240185 (application Ser. No. 12/398,904), entitled, "Dressing and Method for Applying Reduced Pressure To and Collecting And Storing Fluid from a Tissue Site," which is incorporated herein for all purposes, may be used. In another embodiment, the drape 106 may be used to form a wound dressing that is used without reduced pressure and may be used without a distribution manifold.

In the reduced-pressure treatment system 100, either through production in the sealed space or by delivery through the reduced-pressure delivery conduit 124, reduced pressure is realized in the sealed space 118. The reduced pressure may be for reduced-pressure therapy or for removal of fluids. Reduced pressure refers to a pressure less than the ambient pressure at a tissue site 102 that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. As previously noted, in some applications, no reduced pressure is used and only a wound dressing that includes the drape 106 is utilized.

The inclusion of the H-PDLC device 108 as an aspect of the drape 106 allows for an indication—qualitatively or quantitatively—of the presence of strain. When the drape 106 is under stress that results in strain, the H-PDLC device 108 will provide a change in a visual appearance as will be described further below. The H-PDLC device 108 may be calibrated such that certain colors or appearances correspond to certain reduced-pressure ranges. As previously mentioned, identifying or even quantifying strain (or stress) has advantages.

In operation of the illustrative reduced-pressure treatment system 100, the distribution manifold 110 is placed proximate to the tissue site 102. The tissue site 102 and distribution manifold 110 are then covered with the drape 106 to form the sealed space 118. If not already applied (pre-installed on the drape 106), the reduced-pressure interface 120 is fluidly coupled to the sealed space 118 and to the reduced-pressure delivery conduit 124. Reduced pressure is delivered through the reduced-pressure delivery conduit 124 to the sealed space for reduced-pressure treatment or fluid removal. During application of the drape 106, one may observe if too much force has been applied by evaluating the drape 106 color or other visual appearances. For example, the drape 106, and specifically the H-PDLC device 108, experiences a red shift, a blue shift, a polarization change, light intensity change, or another visual change if strained beyond a threshold. When reduced pressure is applied, stress may be applied to the drape 106 by the action of the reduced pressure resulting in a strain, and in response, the drape 106 may change color or further change color or other visual appearances.

When drape 106 is used as a dressing, an optional absorbent layer or other wound-filler material may be placed proximate to the tissue site 102. The drape 106 is then used to cover the tissue site and the optional absorbent layer or other material if used. As before, if the dressing is applied with stretching of the drape 106 beyond a threshold, the visual appearance of the drape 106 will change. For example, the drape 106, and specifically the H-PDLC device 108, experiences a red shift or blue shift or a polarization change or another visual change. In addition, if during use, the dressing is stretched more than a threshold, e.g., five percent or ten percent, the drape 106 will change visual appearance.

The H-PDLC device 108 and other devices using H-PDLC will now be presented. In general terms, the H-PDLC device 108 or other devices herein include layers of liquid crystal (LC) droplets in a polymer matrix and may be used as a reflective strain gauge or detector. Strain is observed by a change in the nature of the light reflected or transmitted from the surface of an H-PDLC-containing film. Layers of the H-PDLC film may be positioned in a device such that a force applied to the film changes the wavelength of the reflected light. This is achieved when the applied strain causes the distance between the LC layers to expand or contract. The change in wavelength may be a blue shift or a red shift depending on expansion or contraction. Other embodiments may involve a change in polarization.

The H-PDLC film has a reflection or transmission grating capable of reflecting or transmitting light of a selected wavelength. The H-PDLC film may include a means for adhering the H-PDLC film to a surface of a polymer layer of the drape (e.g., drape 106 in FIG. 1) or other device (e.g., pressure-indicating devices 814, 820, 822, 824 (FIG. 14); pressure-indicating device 914 (FIG. 15); or pressure-indicating device 1009 (FIGS. 16-17)) for monitoring the strain at the surface or at a particular site. The H-PDLC film may also be laminated within polymer layers or otherwise included in the drape or other devices. For pressure-indicating devices, the H-PDLC may cover a window and may be coupled to a polymer layer as needed to create a desired tensile strength.

Figure 3:
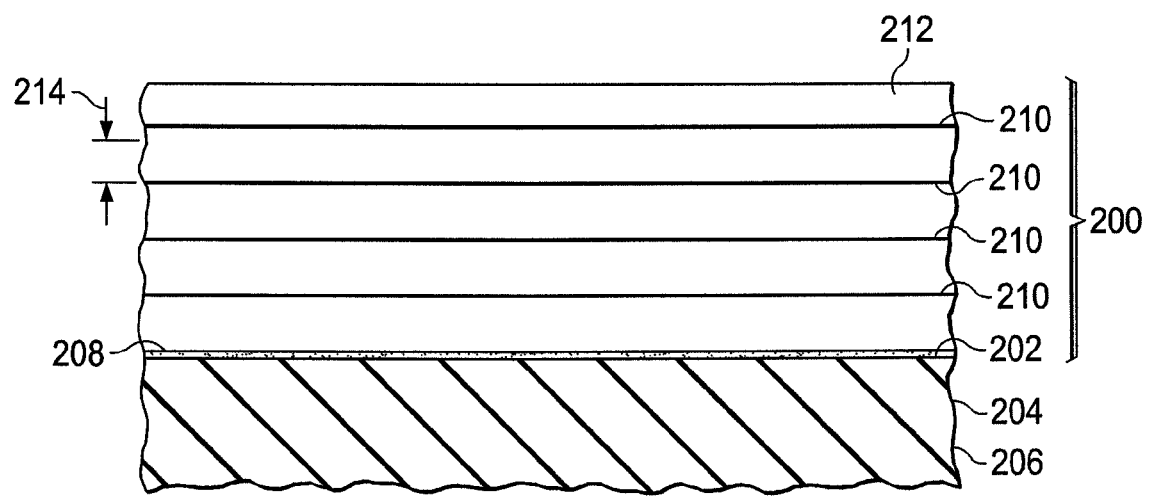
FIG. 3 is a schematic cross section of an illustrative embodiment of a holographically-formed polymer dispersed liquid crystal (H-PDLC) device attached as part of a drape.

Referring now primarily to FIG. 3, an illustrative embodiment of an H-PDLC film 200 is presented such as forms the H-PDLC device 108 of FIGS. 1 and 2 and other embodiments herein. The H-PDLC film 200 includes a reflection grating capable of reflecting light of a selected wavelength. As used herein, "reflection grating" means a periodic array of liquid crystal (LC) droplet planes having an orientation and layer spacing sufficient to reflect light of a selected wavelength that is incident on the surface of the grating. The strain experienced by the drape or other device in which the H-PDLC film 200 is included or attached is transmitted to the H-PDLC film 200. In response, the H-PDLC film 200 alters the reflective light properties of the H-PDLC film 200.

The change in the reflective light properties of the H-PDLC film 200 is representative of, and proportional to, the strain experienced by the drape or other device. The change in the light reflective properties may be in the intensity of the reflected light, e.g., an "on-off" modality, or it may be in the wavelength of the reflected light, e.g., a wavelength shift. The change in the reflected light may be observed visually in those cases where the shift is dramatic enough to be observed by the human eye. Alternatively, the strain in the drape or other device may be observed instrumentally by monitoring the intensity of the reflected light using a photodiode, observing a wavelength shift using a spectrometer or other suitable instrument, or by observing a polarization-dependent shift in the reflected light by incorporating an analyzer between the H-PDLC film 200 and the detector.

Figure 4A:
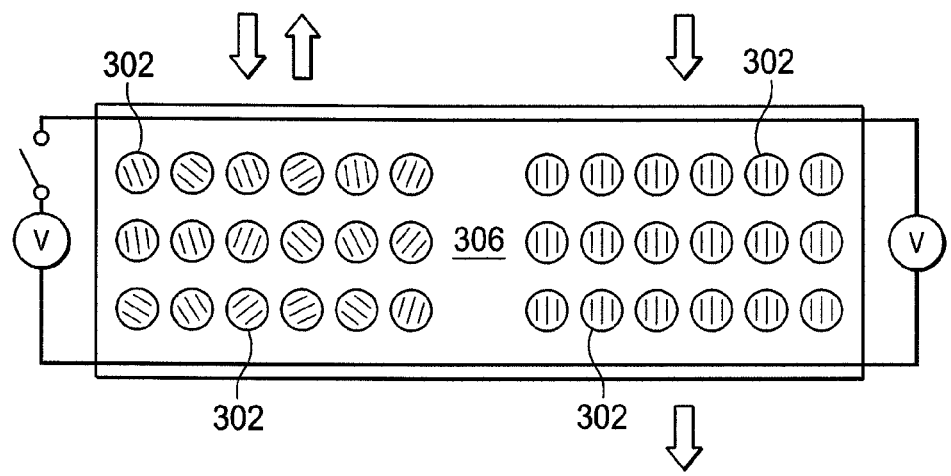
FIG. 4A is a schematic diagram showing a reflective H-PDLC device in two states.
Figure 4B:
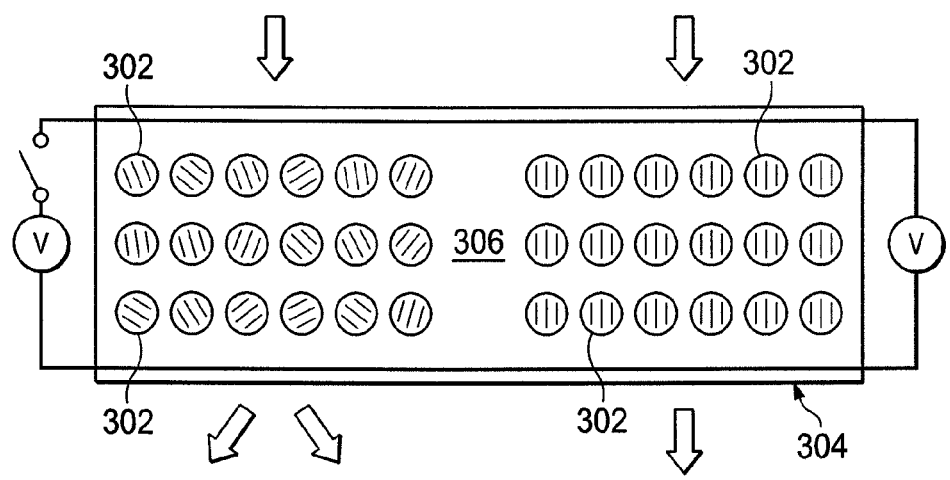
FIG. 4B is a schematic diagram showing a pass-through (transmission) H-PDLC device in two states.

H-PDLC films are phase-separated compositions formed under holographic conditions. Instead of random arrangement of LC droplets, holographic exposure induces a periodic array of LC droplets and matrix polymer planes, as shown in FIGS. 4A and 4B. Upon illumination with holographic light, the monomer diffuses to highlight intensity regions where the monomer polymerizes. The liquid crystal remains in the dark regions and phase separates into small droplets 302 on the order of nanometers, e.g., 10-200 nm, in ordered, stratified layers 304. The actual phase-separated morphology varies dependent upon the particular liquid crystal and the relative composition of the liquid crystal and matrix polymer 306 used. For lower liquid crystal concentrations, spherical or ellipsoidal LC droplets are localized in stratified layers and are completely surrounded by matrix polymer 306. At higher liquid crystal concentrations, connectivity between the LC droplets may be observed. Morphology of the resultant composition also depends on the polymer (composition, molecular weight, or other variables). For example, higher molecular weight polymers tend to favor phase-separation.

If the refractive index of the LC droplet planes or stratified layers 304 ($n_{LC}$) is different from that of the matrix polymer 306 planes ($n_p$), light of a specific wavelength is reflected by the periodic modulation in the refractive index, which is illustrated in the left portion of FIG. 4A. If $n_{LC}$ is equal to $n_p$, the periodic refractive index modulation disappears and the incident light is transmitted through, as is illustrated in the right portion of FIG. 4A. The resulting optical interference pattern reflects at the Bragg wavelength, $\lambda=2*n*d*\sin\theta$, where n is the index of refraction, $\theta$ is the angle between the substrate and viewing direction, and d is the spacing between the LC layers. The interference pattern can be selected to form Bragg gratings that can reflect any visible light. The reflection intensity is determined by the effective refractive index of the LC droplet planes. The Bragg reflection occurs in either the reflection mode (FIG. 4A) or diffraction mode (FIG. 4B) depending on the orientation of the Bragg grating. This, in turn, is dependent upon the beam geometry during phase separation.

It is understood that in instances where reference is made to reflection gratings, a transmission grating may be used. As used herein, "transmission grating" is a periodic array of LC droplet planes having an orientation and layer spacing sufficient to diffract light and to transmit light of a selected wavelength. In those instances it is desirable that the device (e.g., pressure-indicator) be translucent so that changes in the transmitted light are observable.

The adhesive that may be used to couple the H-PDLC film to other portions of the drape may be any material which forms a surface conforming bond between two substrates. The adhesive desirably transfers strain from the drape to the H-PDLC film to thereby deform the film with the resultant change in reflected light. The adhesive should be sufficiently compliant so that the adhesive does not interfere with the transmission of strain from the surface of the other drape components or device components to the H-PDLC film. The desired materials properties for an adhesive include a low elastic modulus, a high yield strength, high adhesion, and a high coefficient of friction, i.e., the interfaces between the adhesive and device and between the adhesive and H-PDLC film do not slip. The adhesive also may be relatively temperature-insensitive, that is, the adhesive may possess a low thermal expansion co-efficient and may be largely unaffected by water (moisture-insensitive) for those applications where the gauge is to be used outdoors, in moist environments, or in temperature extremes. As previously noted, in the alternative, the H-PDLC may be sandwiched between polymer layers.

Turning again primarily to FIG. 3 and to FIGS. 4A-4B, the structure and operation of the H-PDLC film 200, or reflective strain gauge, is further described. The H-PDLC film 200 is coupled to the first side 202 of a polymer layer 204 of a drape 206 (or device). The H-PDLC film 200 may be coupled using an adhesive layer 208. The H-PDLC film 200 has liquid crystal (LC) layers 210 in a matrix polymer 212. The stratified arrangement of LC layers 210 in the matrix polymer 212 gives rise to a reflection grating that reflects a particular wavelength of light. The exact wavelength is determined by the size of the spacing between the LC layers 210, indicated by dimension 214. The liquid crystal layers 210 are shown in FIG. 3 at an orientation substantially parallel to the drape 206 (or device). The LC layers 210, however, may have any desired orientation and may be located, for example, perpendicular to or at any other intermediate angle with respect to the polymer layer 204. The H-PDLC film 200 may be any conventional film capable of reflection of a selected wavelength of light. It should be understood that the number of LC layers 210 is shown schematically and any number of layers may be used in the H-PDLC film 200. For the purposes of simplicity, only a few layers are shown.

Figure 5:
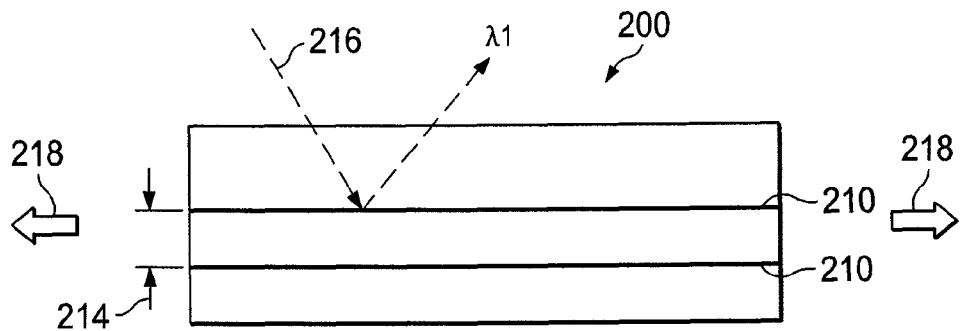
FIG. 5 is a schematic cross section of an illustrative embodiment of an H-PDLC device in an unstrained state.

The shift in wavelength with strain is a function of the extent of d-spacing contraction or expansion of the LC layers 210. For a tensile stress applied along the length of the H-PDLC film 200 and the LC layers 210 as are shown in FIG. 5, the d-space contraction may be quantified to a first approximation by $dL/L=-v dW/W$, where L is the sample length in the direction of pulling, W is the width of the sample perpendicular to pulling, and v is Poisson's ratio. Poisson's ratio may have a value between −1 and +0.5. Typical values for polymeric materials lie in the range of 0.3-0.5. Since the peak reflected wavelength of an H-PDLC film 200 is related to the spacing between LC layers 210, the percent change in film thickness of the sample is equal to the percent change in wavelength. Thus, $dL/L=-v d\lambda/\lambda$.

Figure 6:
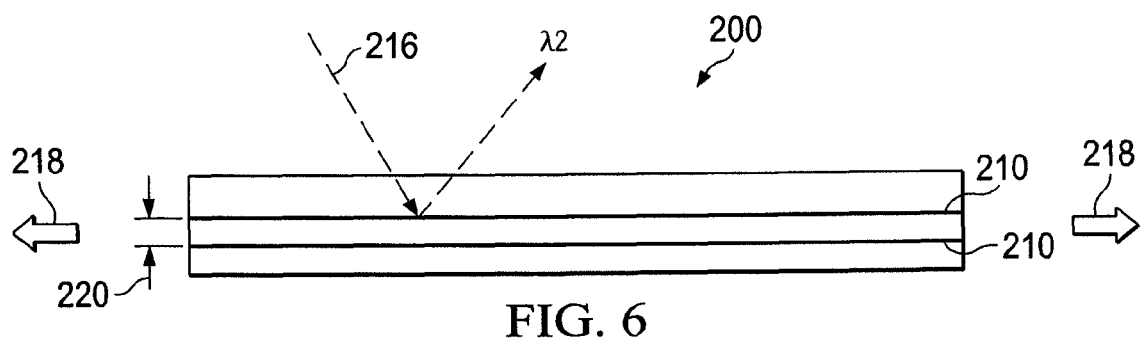
FIG. 6 is a schematic cross section of the illustrative embodiment of the H-PDLC device of FIG. 5 shown strained by a tensile force (strained state)
Figure 7:
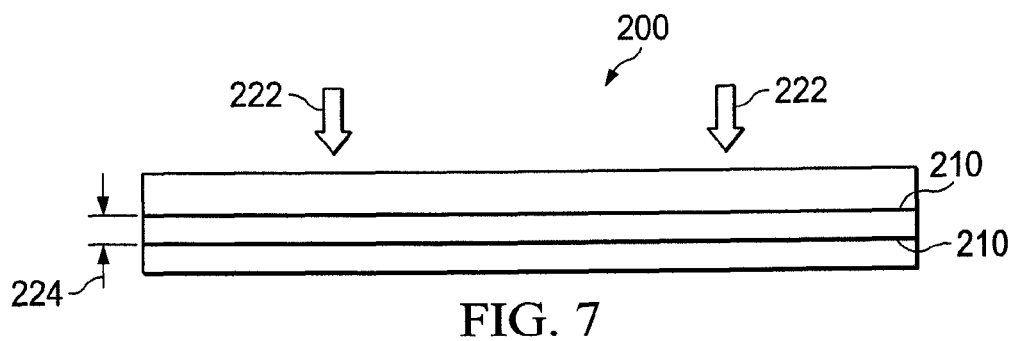
FIG. 7 is a schematic cross section of the illustrative embodiment of the H-PDLC device of FIG. 5 shown strained by a compressive force.

Referring now primarily to FIGS. 5-7, the figures illustrate the basis for the observed wavelength shift in the H-PDLC films 200. Referring initially to FIG. 5, in the unstrained state, the liquid crystal (LC) layers 210 have a spacing "d" indicated by dimension 214. Light 216 incident on the H-PDLC film 200 is reflected at a wavelength $\lambda_1$ that is representative of the d-spacing of the LC layers 210 based on the Bragg equation: $\lambda=2*n*d*\sin\theta$.

Referring now primarily to FIG. 6, when the drape or device on which the H-PDLC film 200 is attached is strained, such as by application of a tensile force as indicated by large arrows 218, the strain is transmitted through the drape or device into the H-PDLC film 200. In some devices, a pressurized gas may act directly on the H-PDLC film 200, e.g., when covering a non-conformable window frame such as that shown in FIG. 14. The strain may be applied when, for example, a reduced pressure is applied to the sealed space, when the patient moves, when the drape is applied, when a positive pressure applied with the installation of a fluid, or other circumstances.

Under the tensile force 218, the H-PDLC film 200 is stretched and the film thickness contracts, with a corresponding contraction of the LC layers 210. As a result, the H-PDLC film 200 develops a new d-spacing indicated by dimension 220. The new d-spacing 220 gives rise to reflection of light of a different wavelength $\lambda_2$. With a contraction of the d-spacing, a shift of the reflected light towards the blue region in the visible spectrum (blue shift) is observed for the same viewing angle.

Referring now primarily to FIG. 7, a compressive force, indicated by large arrows 222, is applied to the H-PDLC film 200. The compressive force 222 may also give rise to a new d-spacing indicated by dimension 224 and resulting in a blue shift in the reflected light. Thus, H-PDLC films 200 may also be used in pressure-sensing devices. If the H-PDLC film 200 is suspended, as in a window, the compressive force may stretch as well as compress the LC layers 210.

Figure 8:
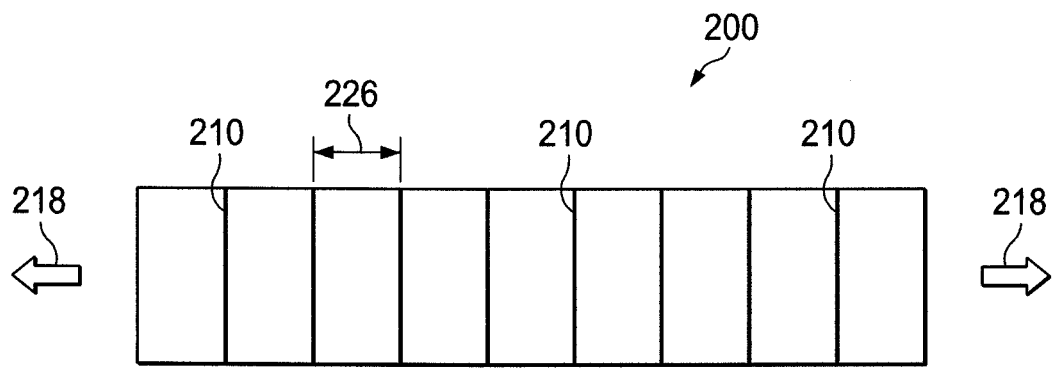
FIG. 8 is a schematic cross section of an illustrative embodiment of an H-PDLC device having liquid crystal (LC) planes orthogonal to a tensile force.
Figure 9:
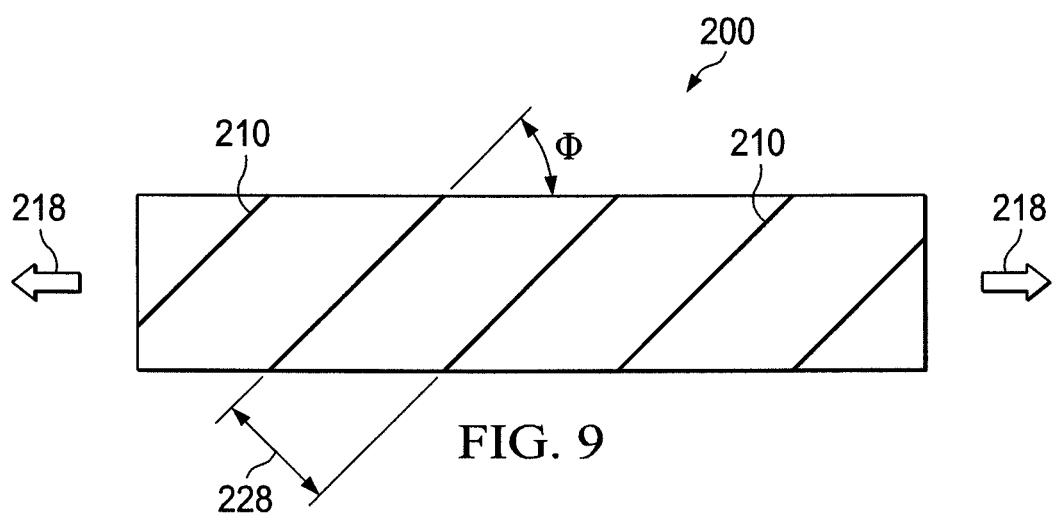
FIG. 9 is a schematic cross section of an illustrative embodiment of an H-PDLC device having liquid crystal (LC) planes angled with respect to a tensile force.

Referring now primarily to FIGS. 8 and 9, the figures illustrate circumstances in which the LC layers 210 may be expanded rather than contracted upon application of a tensile force. In FIG. 8, the LC layers 210 have a vertical orientation vis-à-vis the tensile force 218. The tensile force 218 urges the LC layers 210 outward and may give rise to an expansion of the d-spacing 226 between LC layers 210. The expansion between LC layers 210 results in a shift to higher wavelengths, i.e., a red shift. The H-PDLC film 200 is, thus, set up in a transmission mode due to the perpendicular orientation of the LC layers 210. The transmitted light, however, would experience the same wavelength shift as described above for reflected light. As in the reflection mode, the wavelength shift is proportional to strain experienced in the drape or device.

Referring now primarily to FIG. 9, the LC layers 210 are not in alignment with or orthogonal to the direction of the applied tensile force 218. The tensile force 218 is applied at an angle θ with respect to the LC layers 210, where θ is the angle between the vectors of the applied force 218 and the LC layers 210. The change in d-spacing represented by dimension 228 (and the resultant wavelength) is non-linear. The response of the LC layers 210 to the applied force is complex because both a compressive and tensile component are present.

At low θ, deformation is due primarily to Poisson contraction, and the fractional wavelength shift is approximately one-half the strain in the sample. At high 0, the fractional shift is approximately equal to the strain and is therefore more sensitive. It may, however, be more difficult to measure a shift in wavelength reflection under these conditions. At some intermediate angle and for a given stress vector, the red shift due to stretching of the LC layers 210 will be somewhat balanced by the blue shift due to Poisson-type contraction and an H-PDLC film 200 may be obtained that is substantially insensitive to stress in one direction. A wavelength shift may then be observed, but only in a direction substantially orthogonal to that which is stress-insensitive (a blue-shift would occur due to LC layer contraction). The differing sensitivities of the H-PDLC film 200 to stress in different directions permit the design of H-PDLC films 200 in which the direction, as well as the magnitude, of strain may be determined.

Information regarding orientation of the LC layer 210 is useful in determining not only the existence of strain but its directionality. As discussed herein, the directionality of the applied stress and the orientation of the LC layers 210 can result in either a contraction, expansion or no change of the LC layer spacings (dimensions) 214, 220, 224, 226, 228. Moreover, some LC layer 210 orientations are more sensitive than others to contraction or expansion of the d-spacing. This can provide valuable information as to the forces experienced by the drape or device.

It may be additionally possible to identify where on the drape or device surface the stress is experienced. For example, if the strain is experienced locally on the surface of the drape, only a subsection of the H-PDLC film 200 associated with the drape or device surface would be subjected to the tensile or pressure forces which alter the reflection properties of the H-PDLC film 200. By observing the region of the H-PDLC film 200 undergoing a wavelength shift or change in visual appearance, the strain site may be identified.

In those circumstance where the material characteristics of the H-PDLC film 200 are well documented, quantitative as well as qualitative information regarding strain may be obtained. For a polymer film in tension, the applied force (stress) may be proportional to strain and may be related to the strain experienced in the drape or device. For small deformations (i.e., less than 10% strain), the engineering stress may be defined by the following: $stress_{eng}=E^* strain_{eng}$, where E is Young's modulus. For larger strains, a more accurate relationship may be defined by the following: $stress_{true}=stress_{eng}(1+strain_{eng})=E^*strain_{true}$, where $strain_{true}=\ln(1+strain_{eng})$. Note that this permits determination of the stress (and strain) in the H-PDLC film 200, which may not be the same as the stresses in the drape or device.

Uniaxial extension of a reflective H-PDLC film not only shifts the reflected wavelength, it also introduces a polarization dependence onto the observed reflected light. Polarization is manifested in differences in peak reflected wavelength and in the reflection efficiency for light polarized parallel (pi) and perpendicular (sigma) to the tensile axis. The polarization effect arises when the stresses on the film are sufficient to deform the LC droplets into prolate ellipsoids with the long axis aligned parallel to the tensile axis. The most energetically favorable droplet configuration for a prolate ellipsoid for homogeneous anchoring of the LC to the polymer is bipolar, with the symmetry axis of the droplet parallel to the long axis. For small strains, e.g., less than 3%, the polarization effect is slight. At higher strains, however, molecular orientation of the LC droplets occurs in addition to the d-spacing contraction previously discussed. The strain regime which is most likely to be monitored by the film is in the range of 1-20%, and so the polarization effect is likely to be observed and to be a factor in interpreting the information obtainable from the film.

For an LC with a positive birefringence, the refractive index of the LC droplet is greater parallel to the symmetry axis than perpendicular. In the unstrained state, the symmetry axes of the droplets are oriented randomly throughout the film and the modulation of the refractive index through the film is the same both parallel and perpendicular to the tensile axis. In the strained state, the alignment of the droplets means that the average refractive index and the index amplitude modulation are greater parallel to the tensile axis than perpendicular. The difference in profiles accounts for both the peak wavelength being lower for light polarized perpendicular and the lower reflection efficiencies for the sigma-polarized state.

In the sigma-polarization state, the change in refractive index is small because the average refractive index of the droplets is closer to the ordinary refractive index, $n_o$, and therefore more closely matches the polymer ($n_o \approx n_p$). In the pi-state, the refractive index is weighted more towards the extraordinary refractive index, $n_e$, and the average refractive index is higher, thus increasing the optical path length between planes relative to the sigma state and increasing the peak reflected wavelength. In the pi-state, the amplitude of the refractive index modulation is also greater, resulting in greater efficiencies than the sigma-state.

Figure 10:
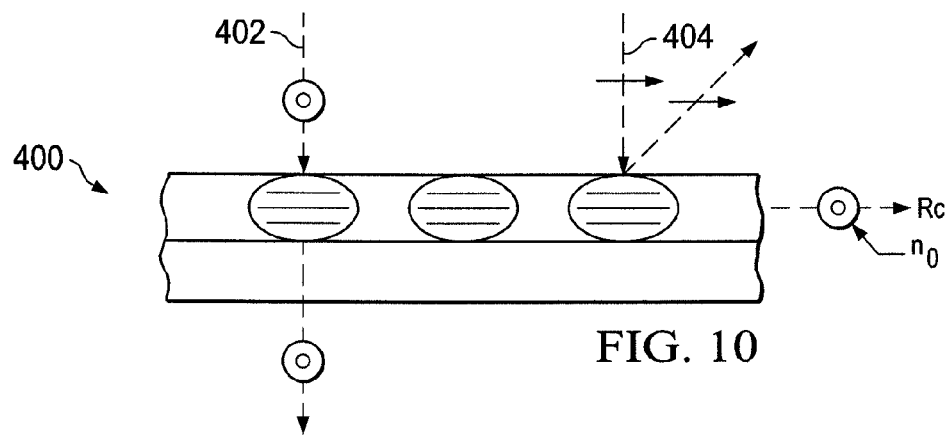
FIG. 10 is a schematic cross section of an illustrative embodiment of a polarization-sensitive H-PDLC device shown in two states.

Referring now primarily to FIG. 10, an H-PDLC film 400 may include a polarization-dependent H-PDLC film as described above. In matrices where $n_o \approx n_p$, sigma-polarized light is transmitted through the film, while pi-polarized light is reflected. Use of polarized light provides an H-PDLC film, or visual strain gauge, with an "on-off" indicator for surface strain, as compared to the "blue-green" indicator (or the like) for non-polarized H-PDLC films. By way of example, the H-PDLC film 400 may have an average refractive index very close to that of the matrix polymer in the unstrained state and an average refractive index approaching $n_e$ in the strained state. Because of the similarity of the refractive indices, no reflection grating is perceived by incident light in the unstrained state and light is transmitted through the H-PDLC film 400.

When the H-PDLC film 400 is stressed, however, the H-PDLC film 400 deforms and the LC droplets molecularly orient to form polarized droplets having a higher refractive index than the surrounding matrix polymer. And, the reflection grating suddenly forms which reflects light of the selected wavelength. If the sample is illuminated with sigma-polarized light (arrow 402) as shown on the left-hand portion (for the orientation shown) of FIG. 10, no reflection is observed. If the light is illuminated with pi-polarized light (arrow 404) as shown on the right-hand portion (for the orientation shown) of FIG. 10, a reflection is observed. Monitoring for an on-off indication may be easier in some circumstances than monitoring for a colorshift.

Polarization-dependent light reflection provides additional advantages, such as increased reflection efficiency, and provides information on the directionality of the strain. Information regarding strain directionality may be obtained even if there is no discernible wavelength shift of the reflected light. For example, a film such as that shown in FIG. 9 may have LC planes at an angle θ that is stress-insensitive, that is, the d-spacing remains unchanged when stressed. Even so, the LC droplets may respond by aligning with the applied stress. Molecular alignment may be observed by scanning the film with a polarizer and noting the angles of increased intensity.

Figure 15:
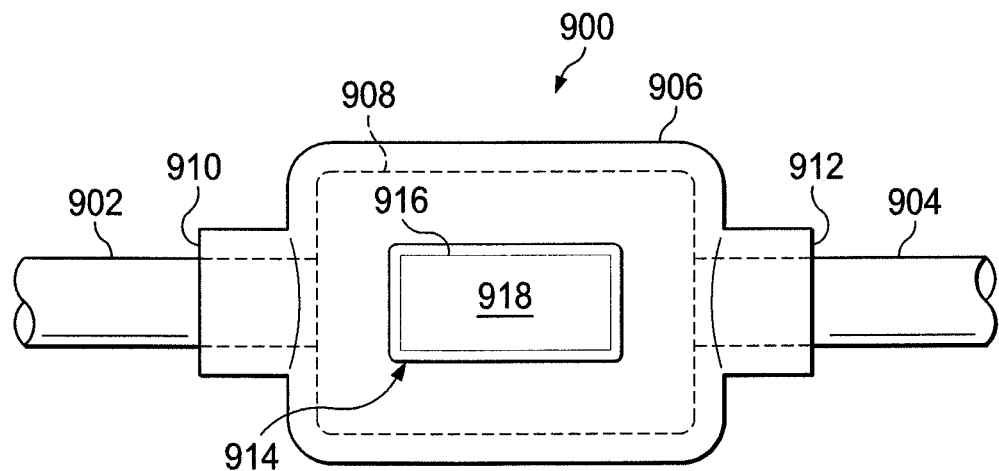
FIG. 15 is a schematic plan view of an illustrative embodiment of a conduit connector for fluidly coupling medical conduits, wherein the conduit connector has a pressure-indicating device that includes an H-PDLC device.

In addition, polarized H-PDLC films 400 formed by stretching could be used to form polarization gratings. When unpolarized light illuminates the polarized H-PDLC films 400, sigma-polarized light will pass through the film without deflection, while pi-polarized light is reflected. Thus, only sigma-polarized light can pass through the film and can thereby serve as a polarizing light filter. This may be more useful on windows of devices, e.g., non-conformable window 916 (FIG. 15).

In some embodiments, the H-PDLC film includes aspected particles made up of the H-PDLC materials randomly dispersed in a supporting polymer which may be the same as that used in the H-PDLC aspected particles, or different. The matrix should, however, exhibit the desired response to applied strain; that is, it should be elastic, have high yield strength and a high strain tolerance to avoid failure under the anticipated use conditions. The aspected particles contain at least one dimension which is large with respect to the remaining dimension(s). Due to the aspected nature of the particles, the particles will rotate or otherwise orient themselves under an applied force so that the particles are aligned. The greater the aspect ratio, the greater the alignment force. In one illustrative embodiment, the aspect ratio (dimension of the long to short dimensions) of the H-PDLC particles is preferably at least 2:1, more preferably at least 4:1, more preferably at least 10:1 and preferable at least 20:1.

Figure 11A:
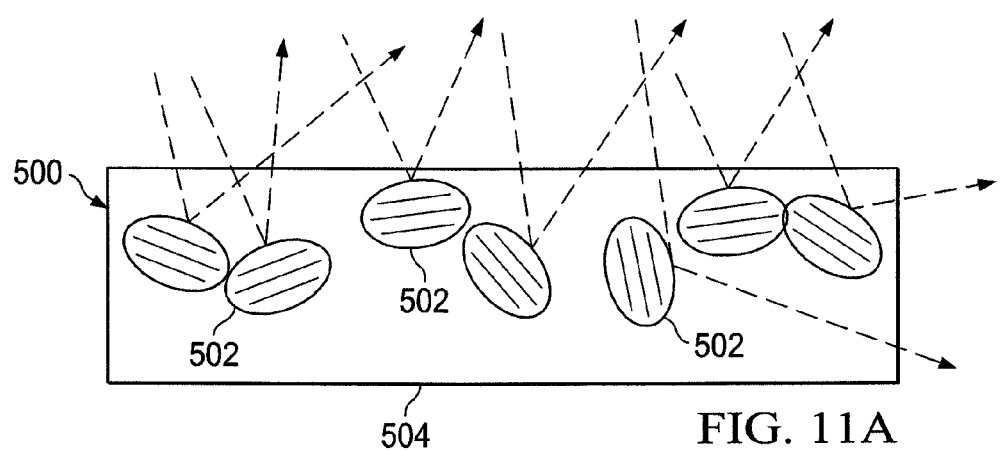
FIG. 11A is a schematic cross section of an illustrative embodiment of a reflective H-PDLC device utilizing aspected H-PDLC particles.
Figure 11B:
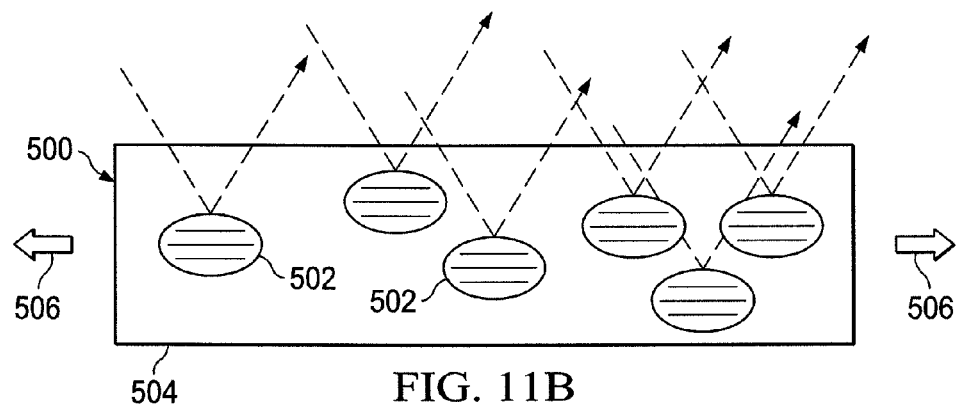
FIG. 11B is a schematic cross section of the reflective H-PDLC device of FIG. 11A shown under stress.

Referring now primarily to FIG. 11A, an H-PDLC film 500 made up of aspected H-PDLC particles 502 in the unstrained state is depicted. The particles 502 are randomly distributed throughout a polymer matrix 504 with no preferred direction of orientation. As a result, the incident light is reflected back to the observer at various angles and the visual effect is indistinct. Under an applied force indicated by arrows 506 in FIG. 11B, the particles 502 orient due to torque on the rod-like particles and the reflected image becomes more intense. The sudden increase in color sharpness and brightness is an indication that the surface of the drape or device has been stressed.

In another embodiment, an H-PDLC film is provided which contains two or more reflection gratings. By using more than one reflection grating, information regarding the tensor or location of strain is provided. The reflection gratings may be located in different H-PDLC films that are layered to form a multilayer H-PDLC film. Alternatively, the reflection gratings may be located within the same film, either by being written into the same portion of the film (overlapping), or by forming different gratings in different and non-overlapping regions of the same film.

In some embodiments, the multiple reflection gratings may have the same d-spacing, yet differ from one another by the orientation of the gratings with respect to the drape or device surface. As described above in FIG. 9, the response of the grating to an applied force depends upon the relationship between the two, which is defined by the angle θ. In some instances, LC layers may be strain-insensitive in certain directions, and so directionality of the applied force may be determined. A single H-PDLC film may include a plurality of gratings at different angles, so that a strain response may be observed by at least one grating in any direction. This increases the useful operation range of the H-PDLC film as well as provides valuable information regarding the tensor of the applied stress. When the gratings reflect at different wavelengths (colors), then the observed, reflected wavelength may be attributed to the appropriate grating and the directionality of the stress is known.

In other embodiments, the H-PDLC film may include films having reflection gratings of different d-spacings, which are capable of reflecting light of different wavelengths. The reflection gratings may be oriented to respond to stress applied in different directions. Depending upon which reflection grating exhibited a shift in reflected wavelength (or demonstrated an "on-off" shift or a polarization shift in the case of polarized films), the H-PDLC film indicates the direction of the applied stress. It may also be possible to arrange the layers such that one reflection grating shifts red under the applied strain, while a second layer shifts blue.

Figure 12:
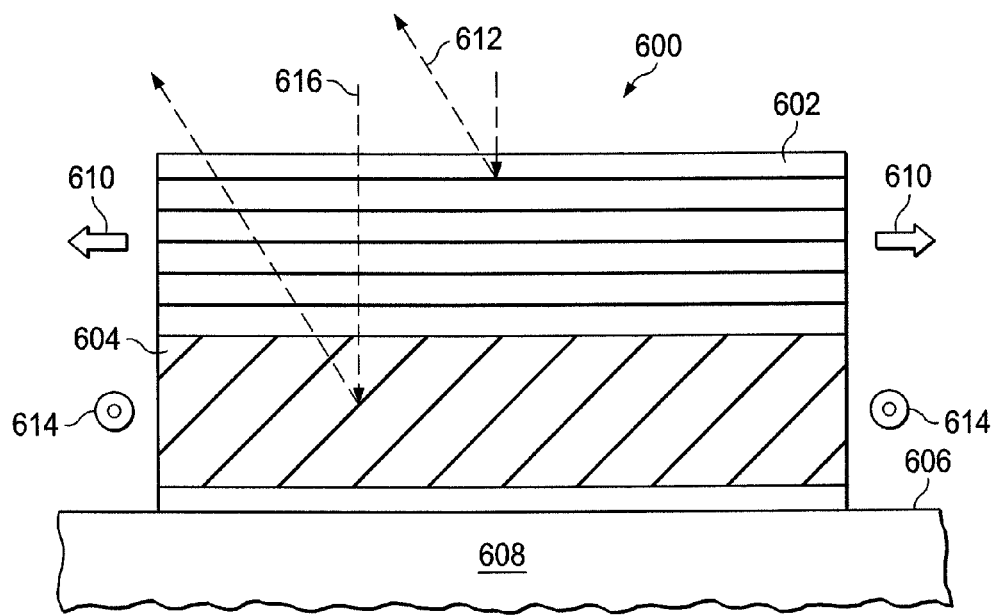
FIG. 12 is schematic cross section of an illustrative reflective H-PDLC device that includes two H-PDLC films with liquid crystal (LC) planes having different orientations.

A multi-layer example is provided in FIG. 12. Referring primarily to FIG. 12, an H-PDLC film 600 has a first H-PDLC layer 602 and a second H-PDLC layer 604. Each H-PDLC layer 602, 604 is made up of a reflection grating at a different orientation with respect to the first surface 606 of the drape or device 608. The first H-PDLC film 602 may include a reflection grating having LC layers at a first angle $\theta_1$ (shown as layers sloping downward and into the plane of the paper) to the surface or side 606 and having a d-spacing to reflect red light. The second H-PDLC film 604, for example, may include a reflection grating having LC layers at a second angle $\theta_2$ to the first surface 606 and having a d-spacing to reflect green light. Each LC layer is stress-insensitive to a different stress vector. Thus, each layer reflects light of a different wavelength and will respond with a shift in their reflection profile when subjected to strains in different directions. As stated above, the different reflection gratings need not be found in different layers. The reflection gratings may be positioned in the same film.

The H-PDLC first layer 602, for example, may be stretched along the length of the LC planes (denoted by large arrow 610). When the drape or device 608 experiences a stress along this axis, the d-spacings of the first H-PDLC layer 602 contract and a blue shift of the red reflecting light 612 occurs. When observing light reflection at the angle defined for first H-PDLC layer 602 a strong shift in the reflected light is observed. The second H-PDLC layer 604, however, is stress-insensitive and light reflecting from it does not shift in wavelength. In contrast, when the first H-PDLC layer 602 is subjected to a stress along the direction noted by arrow 614, no net change of the LC layer spacing occurs and no shift in the reflected light is observed. The second H-PDLC layer 604, however, is greatly effected by this stress vector and a change in the reflected light 616 is observed.

Multiple grating films may be prepared by exposing an H-PDLC precursor film to a plurality of interfering photopolymerizing interference patterns. Each interference pattern results in a reflection grating having characteristic LC plane orientation and d-spacing. These are only some illustrative embodiments for the H-PDLC device.

Figure 13:
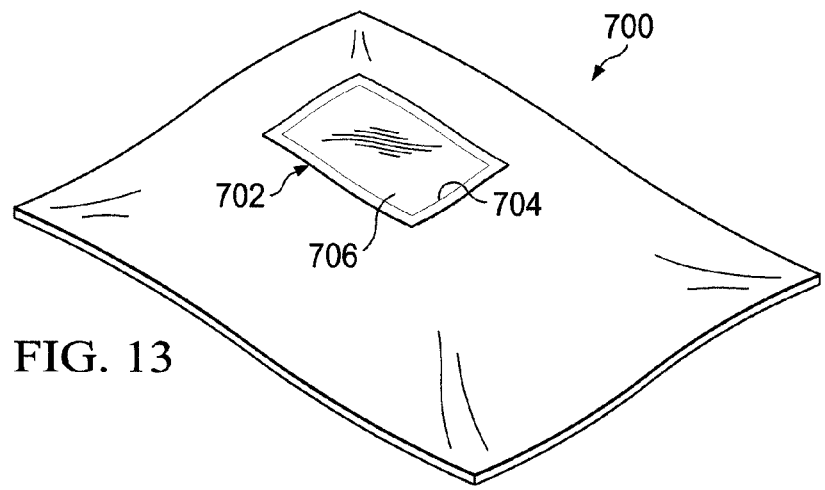
FIG. 13 is a schematic, perspective view of a drape that includes a pressure-indicating device that includes an H-PDLC device.

FIGS. 1-2 present two illustrative embodiments involving the H-PDLC device 108 in a drape 106, but other devices and approaches may be used. For example, the H-PDLC device may be used in a window that is installed in the drape. For example, referring now primarily to FIG. 13, an illustrative embodiment of a drape 700 that may be used as an aspect of a reduced-pressure system, such as the reduced-pressure treatment system 100 of FIG. 1, is presented. In this embodiment, the drape 700 includes a pressure-indicating device 702, or pressure-indicating sensor. The pressure-indicating device 702 includes a non-conformable window frame 704 over which an H-PDLC device or film 706 has been applied. The H-PDLC device or film 706 may include an H-PDLC device of the type previously discussed. Optionally, additional polymer layers may be added to adjust the tensile strength of the H-PDLC device 706. The pressure-indicating device 702 on the drape 700 functions as a pressure sensor for a sealed space, such as sealed space 118 in FIG. 1, created in part by the drape 700.

Thus, when reduced pressure is applied to the sealed space, the pressure differential across (the greater pressure on the side opposite the patient-facing side) the drape 700 causes the drape 700 to experience stress that causes strain. The resultant strain changes the visual appearance of the H-PDLC device 706. In this way, the application of reduced pressure may be confirmed. Similarly, a second, analogous pressure-indicating device (not explicitly shown but analogous to pressure-indicating device 702) may be applied to the drape 700 to indicate positive pressure in the sealed space (greater pressure on the patient-facing side). For example, when a fluid, e.g., a saline wash or liquid medicine, is inserted into the sealed space, the second window experiences a positive pressure on the patient-facing side. When a sufficient amount of the fluid has been introduced, the pressure increases, and the pressure causes a change in the visual appearance of the pressure-indicating device. Thus, the drape 700 may optionally include two or more pressure-indicating devices for measuring reduced pressure and positive pressure or for indicating different pressure ranges of positive pressure or negative pressure.

A plurality of pressure-indicating devices may be used with each having a different pressure threshold at which the visual appearance changes. In this way, the approximate pressure in the sealed space may be indicated.

Figure 14:
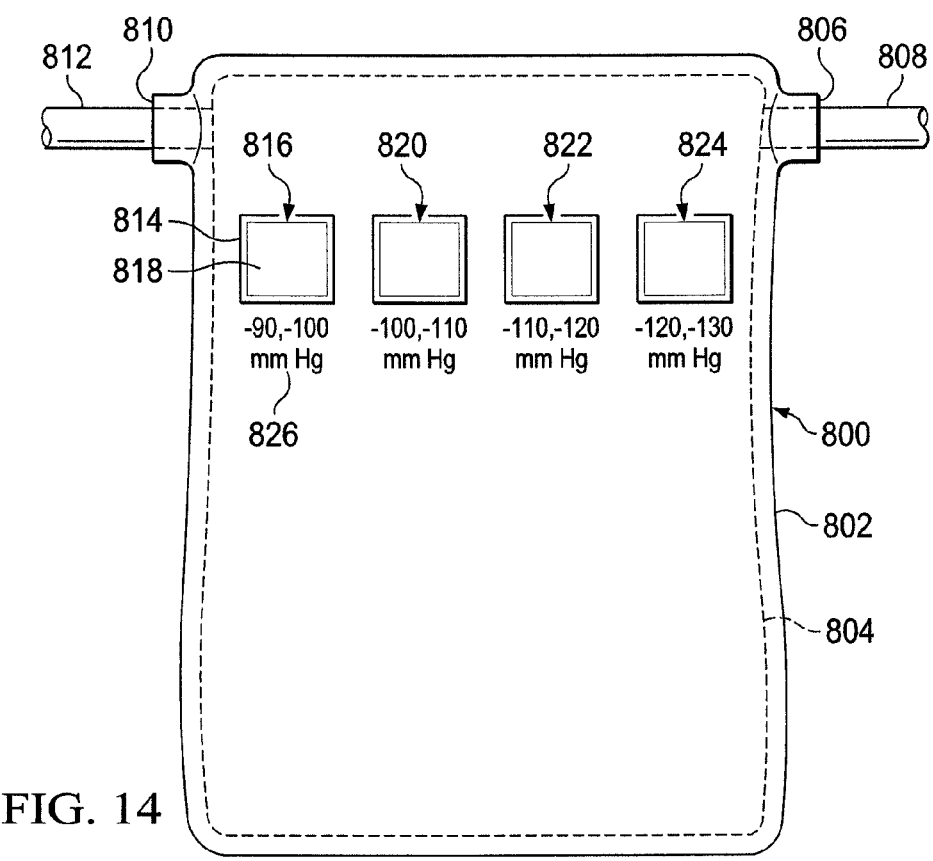
FIG. 14 is a schematic, elevational view of an illustrative embodiment of a canister for receiving body fluids that has at least one pressure-indicating device that includes an H-PDLC device.

Referring now primarily to FIG. 14, a canister 800 for receiving body fluids from a patient is presented. The canister 800 may be used as part of a reduced-pressure treatment system, such as the reduced-pressure treatment system 100 of FIG. 1. The canister 800 has a canister body 802 formed with a fluid reservoir 804 (shown in hidden lines). The canister 800 includes an inlet 806 for receiving a first reduced-pressure delivery conduit 808 from a tissue site (e.g., tissue site 102 in FIG. 1). Reduced pressure may be developed within the canister body 802 or may be delivered through a suction inlet 810 that is coupled to a second reduced-pressure delivery conduit 812.

At least one pressure-indicating device 814 is included on the canister 800 with fluid access to the fluid reservoir 804. The pressure-indicating device 814 includes a non-conformable window frame 816 that is coupled to the canister body 802. The non-conformable window frame 816 is covered by a holographically-formed polymer dispersed liquid crystal (H-PDLC) device 818 of the type previously described. The H-PDLC device 818 of the pressure-indicating device 814 changes visual appearances when experiencing strain caused by reduced pressure (or alternatively positive pressure) within the fluid reservoir 804. The visual appearance occurs when the pressure is within a first range. The strain may be optionally correlated with reduced-pressure ranges in the fluid reservoir 804 to provide a specific range indication corresponding to visual indicia 826.

A plurality of pressure-indicating devices, e.g., pressure-indicating devices 814, 820, 822, 824, may be included on the canister 800. The plurality pressure-indicating devices includes at least two devices, and the pressure-indicating devices change visual appearances for strains of different ranges. In the embodiment of FIG. 14, four pressure-indicating devices are included with each being activated (i.e., changing visual appearance) over a different pressure range. Thus, for example, the first pressure-indicating device 814 changes visual appearance when the reduced pressure in the fluid reservoir 804 is in the range of −90 to −100 mm Hg. The second pressure-indicating device 820 changes visual appearance when experiencing pressure in the range of −100 to −110 mm Hg. The third pressure-indicating device 822 changes visual appearance when experiencing pressure in the range of −110 to −120 mm Hg. The fourth pressure-indicating device 824 changes visual appearance when experiencing pressure in the range of −120 to −130 mm Hg.

In another illustrative embodiment, the non-conformable window frame 816 may itself be in the shape of visual indicia indicating a pressure range associated with the magnitude of strain that causes holographically-formed polymer dispersed liquid crystal (H-PDLC) device for that window to change colors. For example, the window frame itself may form the letters "−100/−110 mm Hg." When a strain indicative of that pressure range is reached, the color (or other visual appearance) of the H-PDLC device visible through the letters changes.

Referring now primarily to FIG. 15, a conduit connector 900 is presented. The conduit connector 900 may used to connect a first medical conduit 902 and a second medical conduit 904 while providing some pressure information. For example, the conduit connector 900 may be used to connect the two portions or segments of the reduced-pressure delivery conduit 124 in FIG. 1 and used as part of a reduced-pressure treatment system, such as the reduced-pressure treatment system 100 in FIG. 1.

The conduit connector 900 includes a connector body 906. The connector body 906 has a chamber 908. The chamber 908 has an inlet 910 for receiving and coupling with the first medical conduit 902 and an outlet 912 for receiving and coupling with the second medical conduit 904. A pressure-indicating device 914 is formed on the connector body 906. The pressure-indicating device 914 comprises a non-conformable window frame 916 covered with a holographically-formed polymer dispersed liquid crystal (H-PDLC) device 918 of the type previously described.

The conduit connector 900 may be used with a reduced-pressure treatment system to provide a visual indication of reduced pressure existing within the reduced-pressure delivery conduit or medical conduits 902, 904. When reduced pressure is present, the reduced pressure is fluidly communicated to the chamber 908 and will cause a pressure differential across the H-PDLC device 918 that places a stress on the H-PDLC device 918. The stress in turn causes a strain to be experienced by the H-PDLC device 918 that changes the visual appearance of the H-PDLC device 918. The change in visual appearances thereby indicates the presence of reduced pressure. The H-PDLC device 918 may be calibrated to change to a particular visual appearance, e.g., a certain color, when the reduced pressure is in a desired pressure range.

Figure 16:
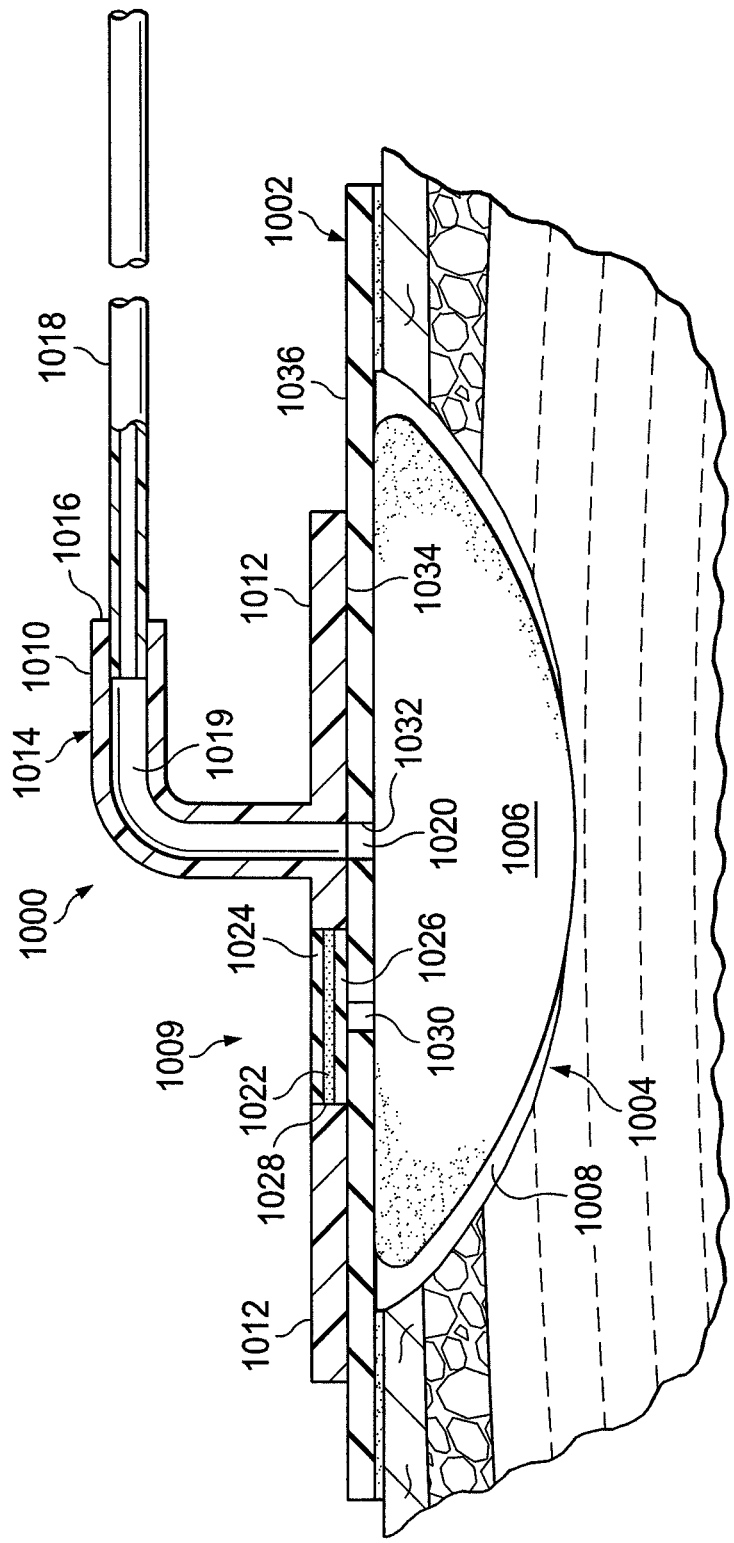
FIG. 16 is a schematic cross section of an illustrative embodiment of a reduced-pressure interface for providing reduced pressure through a drape to a tissue site, wherein the reduced-pressure interface has a pressure-indicating device that includes an H-PDLC device.

Referring now primarily to FIG. 16, a reduced-pressure interface 1000 for providing reduced pressure through a drape 1002 to a tissue site 1004 is presented. The reduced-pressure interface 1000 may be used as part of a reduced-pressure treatment system, e.g., the reduced-pressure treatment system 100 of FIG. 1. The drape 1002 covers a distribution manifold 1006 and forms a sealed space 1008. The reduced-pressure interface 1000 includes a pressure-indicating device 1009 for providing a visual indication of the presence of reduced pressure in the sealed space 1008 or a positive pressure in the sealed space 1008. The pressure-indicating device may be calibrated to indicate a particular pressure range.

The reduced-pressure interface 1000 includes an interface body 1010. The interface body 1010 has a base 1012 and a suction head 1014. The suction head 1014 includes a conduit opening 1016 for fluidly coupling to a reduced-pressure delivery conduit 1018 and a delivery opening 1020 for communicating reduced pressure to the tissue site 1004. A passageway 1019 in the interface body 1010 fluidly couples the conduit opening 1016 and the delivery opening 1020.

At least a portion of the interface body 1010 includes a pressure-indicating device 1009. The pressure-indicating device 1009 comprises a holographically-formed polymer dispersed liquid crystal (H-PDLC) device 1022 of the type previously described having layers of liquid crystal (LC) droplets in a matrix polymer. The H-PDLC device 1022 may be attached to a polymer layer 1024 or sandwiched by polymer layers 1024, 1026. The pressure-indicating device 1009 includes an aperture or non-conforming window 1028 formed in the base 1012 that is covered by the holographically-formed polymer dispersed liquid crystal (H-PDLC) device 1022. An aperture 1030 corresponding to and aligned with pressure-indicating device 1009 may be formed in the drape 1002 to provide fluid communication between the sealed space 1008 and the H-PDLC device 1022 (or the polymer layer 1026 adjacent to the H-PDLC device 1022). Thus, the pressure in the sealed space 1008 is communicated to the H-PDLC device 1022.

In operation, the distribution manifold 1006 is placed proximate to the tissue site 1004 and covered by the drape 1002 to form the sealed space 1008. The reduced-pressure interface 1000 may be pre-installed (installed before use) on the drape 1002 or attached at the time of use. An aperture 1032 is formed in the drape 1002 and the delivery opening 1020 is positioned over the aperture 1032. The reduced-pressure interface 1000 includes an adhesive or other attachment device on a patient-facing side 1034 that attaches the reduced-pressure interface 1000 to a first side 1036 of the drape 1002. The reduced-pressure delivery conduit 1018 is fluidly coupled to the conduit opening 1016. Reduced pressure is supplied to the sealed space 1008.

As sufficient reduced pressure enters the sealed space 1008, the reduced pressure is communicated to the pressure-indicating device 1009. The H-PDLC device 1022 in the pressure-indicating device 1009 experiences a stress from the pressure. Once the resultant strain caused by the stress reaches a calibrated range for the H-PDLC device 1022 (i.e., is greater than a threshold pressure), the H-PDLC device 1022 changes visual appearance. The visual appearance may indicate merely the existence of reduced pressure beyond the threshold pressure or may designate a precise reduced pressure range.

Figure 17:
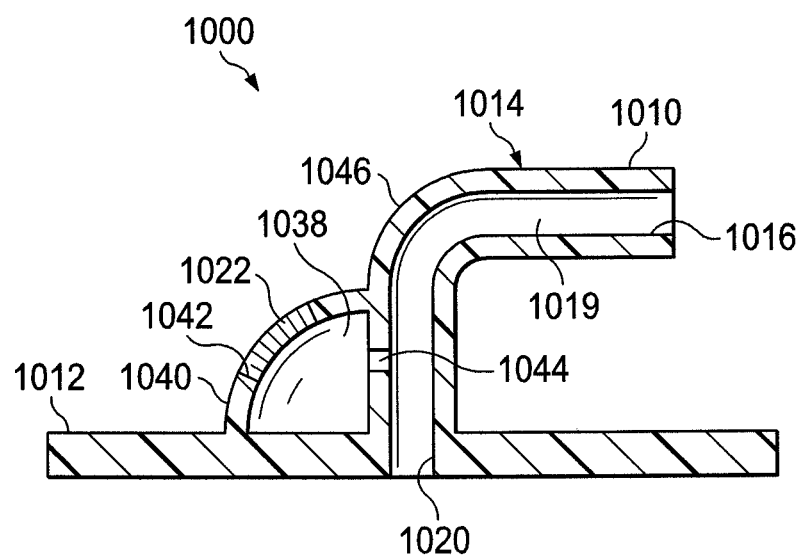
FIG. 17 is a schematic cross section of an illustrative embodiment of a reduced-pressure interface for providing reduced pressure through a drape to a tissue site and having a pressure-indicating device that includes an H-PDLC device.

Referring now primarily to FIG. 17, another illustrative embodiment of a reduced-pressure interface 1000 is presented. The reduced-pressure interface 1000 is analogous in most respects to the reduced-pressure interface 1000 of FIG. 16. Thus, the reduced-pressure interface 1000 includes an interface body 1010 having a base 1012, a suction head 1014, and a passageway 1019. In this embodiment, however, the suction head 1014 includes an assessment chamber 1038 having a chamber wall 1040.

The pressure-indicating device 1009 is formed on the chamber wall 1040. An aperture, or window 1042, is formed on the chamber wall 1040. The window 1042 is covered with a holographically-formed polymer dispersed liquid crystal (H-PDLC) device 1022 of the type previously described to form the pressure-indicating device 1009. The H-PDLC device 1022 may be attached to a polymer layer or sandwiched by polymer layers. Reduced pressure in the passageway 1019 between a conduit opening 1016 and a delivery opening 1020 is fluidly coupled to the assessment chamber 1038 by an aperture 1044 in a passageway wall 1046 of the suction head 1014.

The reduced-pressure interface 1000 of FIG. 17 is used analogously to the reduced-pressure interface 1000 of FIG. 16, except that the pressure-indicating device 1009 receives reduced pressure (or positive pressure) from the passageway 1019. The passageway 1019 is fluidly coupled to a sealed space (e.g., sealed space 1008 of FIG. 16) over the tissue site. The pressure-indicating device 1009 may indicate the existence of stress caused by reduced pressure or by positive pressure when fluids are being delivered.

According to another illustrative embodiment, a method for treating a wound includes preparing the wound and covering the wound with a drape. Preparing the wound may be include cleaning the wound and applying a medicament, such as an antibiotic. The drape comprises a holographically-formed polymer dispersed liquid crystal (H-PDLC) device of the type previously described having layers of liquid crystal (LC) droplets in a matrix polymer. The drape is configured to change visual appearance when subjected to a strain greater than a threshold strain. The method further includes confirming that that the drape has not experienced a change in visual appearance indicative of a strain greater than the threshold strain. The method may also include disposing a wound filler on the wound. The wound filler may be any substance for wicking fluids away from the wound or alternatively or additionally providing moisture to the wound. Example of wound fillers include, without limitation, foam, gauze, hydrocolloid, or felted mat.

Although the present invention and its advantages have been disclosed in the context of certain illustrative embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A reduced-pressure treatment system for treating a tissue site, the system comprising:
    a distribution manifold for disposing proximate to the tissue site;
    a drape for covering the distribution manifold and a portion of intact skin to form a sealed space; and
    a reduced-pressure source fluidly coupled to the sealed space;
    wherein the drape comprises a holographically-formed polymer dispersed liquid crystal (H-PDLC) device having layers of liquid crystal (LC) droplets in a matrix polymer.

2. The system of claim 1, wherein the H-PDLC device covers a window frame.

3. The system of claim 1, wherein the H-PDLC device is operable to change colors when a desired pressure range in the sealed space exists.

4. The system of claim 1, wherein the drape comprises a plurality of laminated polymer layers and wherein the H-PDLC device is disposed between at least two of the plurality of laminated polymer layers.

5. The system of claim 4, further comprising a reflective layer disposed on a tissue-facing side of the H-PDLC device to reflect light back through the H-PDLC device.

6. The system of claim 1, wherein the H-PDLC device comprises a plurality of strips attached to a polymer layer.

7. The system of claim 1, wherein the H-PDLC device comprises a grid attached to a polymer layer.

8. The system of claim 6, wherein the H-PDLC device covers 50 percent or less of a surface area of the drape.

9. A method for treating a tissue site with reduced pressure, the method comprising:
    disposing a distribution manifold proximate to the tissue site;
    covering the distribution manifold and a portion of intact skin with a drape to form a sealed space, wherein the drape comprises a holographically-formed polymer dispersed liquid crystal (H-PDLC) device;
    delivering reduced pressure to the sealed space; and
    monitoring the drape for any changes in visual appearance in the H-PDLC device.

10. The method of claim 9, wherein the step of monitoring comprises using a photodiode, a spectrometer for observing a wavelength shift, or an analyzer for observing a polarization-dependent shift in the reflected light.

11. A drape for covering a tissue site, the drape comprising:
    a first polymer layer;
    a second polymer layer; and
    a holographically-formed polymer dispersed liquid crystal (H-PDLC) device having layers of liquid crystal (LC) droplets in a matrix polymer disposed between the first polymer layer and the second polymer layer; and
    an attachment device coupled to a portion of the drape adapted for removably coupling the drape to skin proximate to the tissue site.

12. The drape of claim 11, further comprising a non-conformable window frame and the H-PDLC device covers at least a portion of the non-conformable window frame.

13. The drape of claim 11, further comprising a plurality of pressure-indicating devices, wherein each of the pressure-indicating devices comprises a window covered by the H-PDLC device, and wherein each of the plurality of pressure-indicating devices is adapted to change visual appearances over a different pressure range.

14. The drape of claim 11, wherein the H-PDLC device comprises a plurality of spaced strips and wherein the spaced strips are disposed on a polymer layer of the drape.

15. The drape of claim 11, wherein the H-PDLC device comprises a grid on a polymer layer.

16. The drape of claim 11, wherein the H-PDLC device covers 50 percent or less of a surface area of the drape.

17. A reduced-pressure interface for providing reduced pressure to a tissue site, the reduced-pressure interface comprising:
    an interface body;
    a conduit opening for coupling to a reduced-pressure delivery conduit, a delivery opening for communicating reduced pressure to the tissue site, and a passageway fluidly coupling the conduit opening and the delivery opening through the interface body; and
    wherein the interface body comprises a holographically-formed polymer dispersed liquid crystal (H-PDLC) device having layers of liquid crystal (LC) droplets in a matrix polymer.

18. The reduced-pressure interface of claim 17, wherein the interface body further comprises a base and a portion of the base comprises the H-PDLC device.

19. The reduced-pressure interface of claim 17, wherein the interface body further comprises a suction head and a portion of the suction head comprises the H-PDLC device.

20. The reduced-pressure interface of claim 17, further comprising:
   a chamber wall forming a chamber and having a window formed on the chamber wall;
   wherein the window is covered by the H-PDLC device to form a pressure-indicating device; and
   wherein the interface body is formed with a passageway having an aperture that fluidly couples the passageway and the chamber.

21. A canister for receiving body fluids, the canister comprising:
   a canister body forming a fluid reservoir;
   an inlet formed on the canister body for receiving a reduced-pressure delivery conduit;
   a window frame formed on the canister body;
   a holographically-formed polymer dispersed liquid crystal (H-PDLC) device covering the window frame; and
   wherein the H-PDLC device is adapted to change visual appearances when experiencing strain within a first range.

22. The canister of claim 21, further comprising a plurality of pressure-indicating devices, wherein the window frame comprises at least one of the plurality of pressure-indicating devices, and wherein at least two of the pressure-indicating devices of the plurality of pressure-indicating devices change visual appearances for strains of different magnitudes.

23. The canister of claim 21, wherein the window frame is a non-conformable window frame indicating a pressure range associated with a magnitude of strain over which the H-PDLC device changes visual appearances.

24. A conduit connector for connecting medical conduits, the conduit connector comprising:
   a chamber in a connector body,
   an inlet fluidly coupled to the chamber for receiving a first conduit, and
   an outlet fluidly coupled to the chamber for receiving a second conduit; and
   a pressure-indicating device formed on the connector body, wherein the pressure-indicating device comprises a window frame covered by a holographically-formed polymer dispersed liquid crystal (H-PDLC) device.

25. A method for treating a wound, the method comprising:
   covering the wound with a drape, wherein the drape comprises a holographically-formed polymer dispersed liquid crystal (H-PDLC) device having layers of liquid crystal (LC) droplets in a matrix polymer and wherein the drape is configured to change visual appearance when subjected to a strain greater than a threshold strain; and
   confirming that that the drape has not experienced a change in visual appearance indicative of a strain greater than the threshold strain.

26. The method of claim 25, further comprising disposing a wound filler on the wound.

\* \* \* \* \*